United States Patent [19]

Huang

[11] Patent Number: 4,464,395

[45] Date of Patent: Aug. 7, 1984

[54] ANTIHYPERTENSIVE COMPOUND 176

[75] Inventor: Leeyuan Huang, Westfield, N.J.

[73] Assignee: Merck & Co., Inc., Rahway, N.J.

[21] Appl. No.: 365,743

[22] Filed: Apr. 5, 1982

[51] Int. Cl.$^3$ .................. A61K 31/195; C07C 129/12
[52] U.S. Cl. ..................................... 424/319; 562/560
[58] Field of Search ................. 562/560; 424/319, 116

[56] References Cited

U.S. PATENT DOCUMENTS

| | | | |
|---|---|---|---|
| 3,679,742 | 7/1972 | Umezawa | 562/560 |
| 3,743,580 | 7/1973 | Umezawa | 562/560 |
| 3,809,759 | 5/1974 | Bocher | 562/560 |
| 3,915,918 | 10/1975 | Wille | 260/112.5 |
| 3,967,770 | 8/1976 | Bumpus et al. | 424/177 |
| 4,061,542 | 12/1977 | Demny | 562/560 |
| 4,173,704 | 11/1979 | Ondetti et al. | 548/336 |
| 4,216,209 | 8/1980 | Bellini et al. | 424/177 |
| 4,220,642 | 9/1980 | Said et al. | 424/177 |

*Primary Examiner*—Michael L. Shippen
*Attorney, Agent, or Firm*—Ernest J. Linek; Salvatore C. Mitri

[57] ABSTRACT

Antihypertensive compound 176 is a natural product amino acid produced by cultivation of a Streptomyces species under controlled aerobic fermentation conditions. The product is also shown to inhibit angiotensin converting enzyme.

3 Claims, 2 Drawing Figures

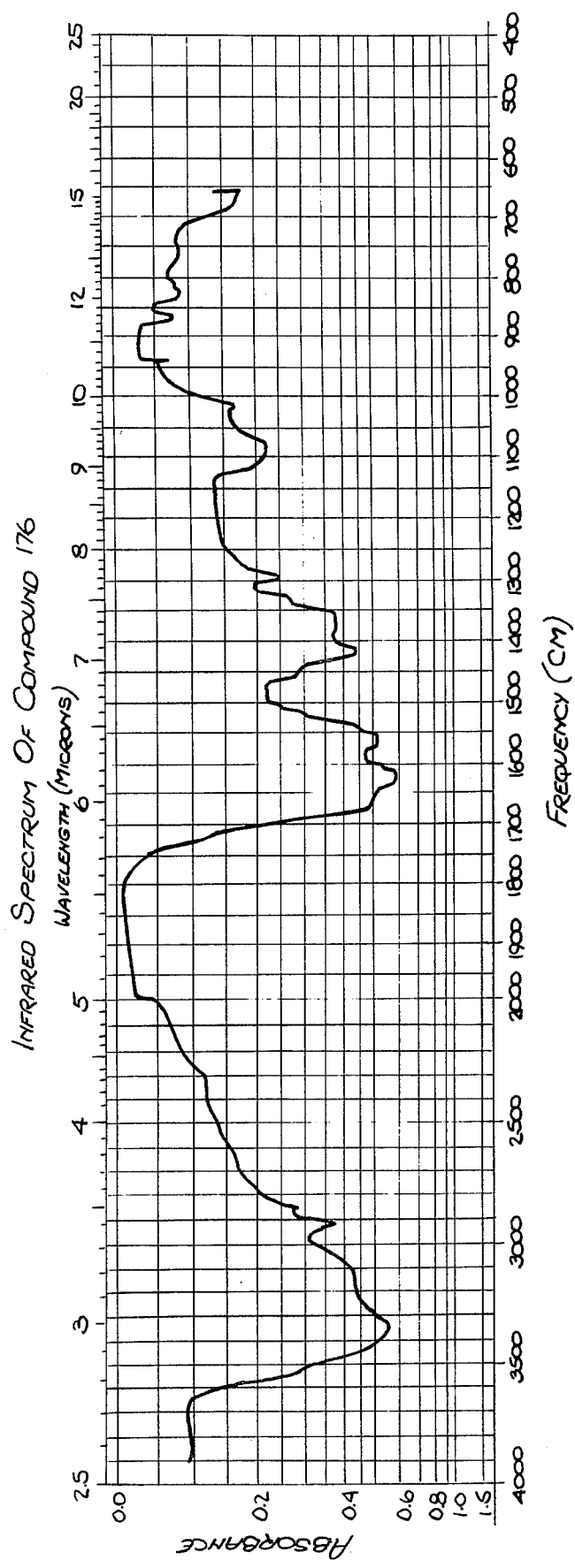
Fig. 2. Infrared Spectrum Of Compound 176

ANTIHYPERTENSIVE COMPOUND 176

BACKGROUND OF THE INVENTION

Polypeptide compounds and other amino acid derivatives useful as antihypertensive agents and angiotensin converting enzyme inhibitors are well known classes of synthetic compounds. See for example, Bellini et al., in U.S. Pat. No. 4,216,209; Bumpus in U.S. Pat. No. 3,976,770; Ondetti et al. in U.S. Pat. No. 4,173,704; and Wille in U.S. Pat. No. 3,915,948. A natural product polypeptide with vasoactive and hypotensive properties has been isolated from the lungs of animals, especially hogs; see, Said et al., U.S. Pat. No. 4,220,642.

SUMMARY OF THE INVENTION

The present invention is directed to the antihypertensive amino acid compound 176 and the production thereof by cultivation in an aqueous nutrient medium of a Streptomyces species, ATCC 39069.

BRIEF DESCRIPTION OF THE DRAWINGS

FIG. 2 is an infrared spectrum of the antihypertensive compound 176.

DETAILED DESCRIPTION

Figure 1:
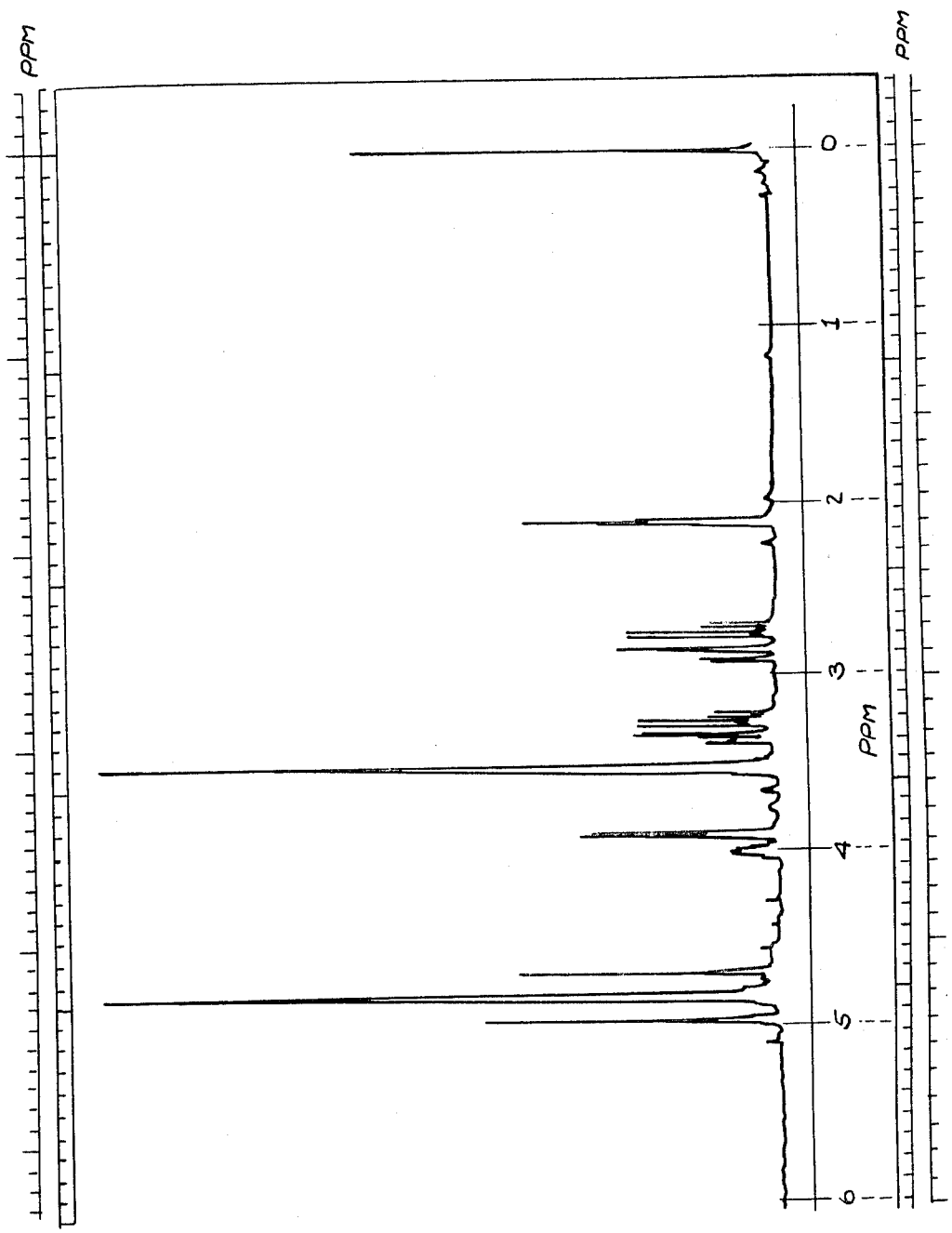
FIG. 1 is a proton NMR spectrum of the antihypertensive compound 176.

The present invention is directed to the natural product amino acid, antihypertensive compound 176, which has the structure:

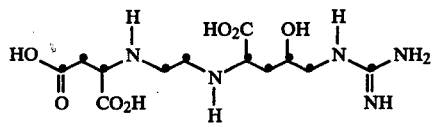

The present invention is also directed to a process for producing the antihypertensive compound 176, characterized by cultivating an antihypertensive compound 176 producing strain of Streptomyces species in an aqueous nutrient medium under controlled aerobic fermentation conditions and isolating the accumulated antihypertensive compound 176 from the cultured broth.

It is to be understood that for the production of the antihypertensive compound 176, the present invention is not limited to the use of the Streptomyces species ATCC 39069. It is especially desired and intended that there be included within the scope of this invention the use of natural or artificial mutants produced from the described organism, or other variants of the genus Streptomyces, insofar as they can produce the antihypertensive compound 176. The artificial production of mutant Streptomyces species from ATCC 39069 may be achieved by a conventional operation such as X-ray or ultraviolet (UV) irradiation of the Streptomyces species ATCC 39069, or by the use of chemical mutagens such as: nitrogen mustards, nitrosoguanidine and the like.

MORPHOLOGICAL AND CULTURAL CHARACTERISTICS OF STREPTOMYCES SPECIES ATCC 39069

The cultural and morphological characteristics described herein have been compared to those descriptions of Streptomyces species in Bergey's *Manual of Determinative Bacteriology*, 8th Edition. The Williams and Wilkins Co.; E. B. Shirling and D. Gottlieb's "Cooperative Descriptions of Type Cultures of Streptomyces", Int. J. Syst. Bact. 18, 69–189, 279–399 (1968); and S. A. Waksman, *The Actinomycetes*, Vol. 2, 1961 The Williams and Wilkins Co. The data shown below confirms the designation of the genus of this microorganism as being Streptomyces.

The cultural characteristics of Streptomyces sp. ATCC 39069 are as follows:

(V=vegetative growth; A=aerial mycelium; SP=soluble pigment)

Morphology: Sporophores form long open spirals, corkscrew-like in appearance. The spirals are formed of chains of spores, more than 15 spores in length. The sporophore are highly branched, forming tufts at ends of aerial mycelia.

Oatmeal agar
 V: Reverse—dark tan
 A: Very pale gray mixed with white and edged with medium gray
 SP: Very light brown
Czapek Dox agar (sucrose nitrate agar)
 V: Reverse—tan
 A: Velvety, off-white. No sporulation
 SP: None
Egg albumin agar
 V: Reverse—light grayish tan
 A: Moderate, grayish white. Very little sporulation
 SP: None
Glycerol asparagin agar
 V: Tan
 A: Moderate, grayish white. Very little sporulation
 SP: None
Inorganic salts-starch agar
 V: Reverse—grayed tan
 A: Light gray and white mixed, edged with soft silver gray
 SP: None
Yeast extract-malt extract agar
 V: Reverse—brown
 A: Light gray mixed with white, edged with dark gray
 SP: None
Peptone-iron-yeast extract agar
 V: Brown
 A: None
 SP: Brown
 Melanin: Positive
Nutrient tyrosine agar
 V: Dark brown
 A: None
 SP: Dark brown
 Decomposition of tyrosine: Tyrosine crystals decomposed
Tyrosine Agar
 V: Reverse—dark brown
 A: Grayish
 SP: Brown
Carbon utilization:
 Pridham-Gottlieb basal medium+1% carbon source;
 +=growth; ±=growth poor or questionable;
 −=no growth as compared to negative control (no carbon source)
Glucose—+
Arabinose—+
Cellulose—−
Fructose—+

Inositol—+
Lactose—+
Maltose—+
Mannitol—±
Mannose—+
Raffinose—+
Rhamnose—+
Sucrose—+
Xylose—+

Temperature range—(Yeast extract-dextrose+salts agar)
28° C.—Good vegetative and aerial growth with sporulation
37° C.—Good vegetative and aerial growth with sporulation.
50° C.—No growth
Oxygen requirement (Stab culture in yeast extract-dextrose+salts agar):
Aerobic All readings were taken after three weeks at 28° C. unless noted otherwise. pH of all media was approximately neutral (6.8–7.2)

A biologically pure sample of the living Streptomyces species has been deposited without restriction in, and made a part of, the American Type Culture Collection, Rockville Maryland, from which it is available under the Accession Number ATCC 39069.

In the present invention, the antihypertensive compound 176 is produced by cultivation of the microorganism, Streptomyces species ATCC 39069 at a temperature range of from about 24° C. to 30° C., preferably 28° C. under controlled aerobic conditions. The composition of the nutrient medium may be varied over a wide range. The essential nutrient ingredients are: a carbon source, a nitrogen source, a phosphorous source, a sulfur source and a source of ions including $Cl^-$, $Na^+$, $K^+$, $Ca^{2+}$ and $CO_3^{2-}$.

Cultivation is most productive under pH conditions of nearly neutral preferably within the range of 6.0–8.0.

Typical sources of carbon include, glucose, lactose, maltose, sucrose, fructose, dextrin, starches, molasses, glycerol, and the like. Typical nitrogen sources include vegetable meals (e.g., soy, peanut, corn, etc.), rice, bran, meal flours, animal viscera, various hydrolysates (casein, yeast, sobyean, etc.), urea and amino acids.

The maximum yield of the antihypertensive compound 176 can be achieved within about 72 to 120 hours, usually is about 96 hours of fermentation under optimum conditions. The inoculum for the fermentation may be provided from vegetative growth in a medium which supports rapid growth of the organism, such as those set out in Table I below.

Following cultivation, the antihypertensive compound 176 may be recovered from the broth by chromatographic means. Generally the cultured fermentation broth is filtered and the filtrate (pH about 7.5) is acidified with an aqueous mineral acid, for example 2.5N hydrochloric acid to pH 3.5 and adsorbed onto an acidic ion-exchange resin such as Dowex 50×4 (200–400 mesh) ammonium cycle ($NH_4^+$) resin and eluted with aqueous 2% pyridine (v/v) after first washing the column with water. Other mineral acids such as $H_2SO_4$, $HNO_3$, $H_3PO_4$ and the like should also prove useful in this application.

The pyridine eluant is collected and concentrated in vacuo and adsorbed onto an acidic ion-exchange resin such as Dowex 50×4 (200–400 mesh) pyridinium cycle resin and eluted stepwise with pyridinium acetate buffers of increasing pH. The active fractions are collected from the pH 4.0–4.5 elution.

The combined fractions are concentrated to about one-half volume, cooled and the antihypertensive compound 176 crystallizes spontaneously from the cold water.

CHARACTERIZATION OF ANTIHYPERTENSIVE COMPOUND 176

The purified antihypertensive compound 176 is obtained as colorless needles from cold water following isolation from the cultured broth.

The product exhibits moderate solubility in water and aqueous lower alkanol solutions (up to 50% v/v) and insolubility in the lower alkanols and the apolar solvents such as hexanes and the like.

As used therein, the term "aqueous lower alkanol(s)" is meant to include the common $C_1$ to $C_4$ straight and branched, saturated alcohols typified by, methanol, ethanol, propanol, iso-propanol, butanol, sec-butanol, tert-butanol and the like. As stated, the compound 176 exhibits moderate solubility in up to a 50% (v/v) aqueous lower alkanol solution. As used herein, the term "apolar solvents(s)" includes those $C_5$ to $C_{10}$ straight and branched, saturated and unsaturated, cyclic and acyclic solvents typified by pentane, hexane, heptane, octane, nonane, decane, cyclohexane, cycloheptane, cyclooctane, the skellysolves A, B, C, D, E, F and G, ligroin, and the like.

Thin layer chromatography Tlc—silica gel E. Merck) using an elution system of butanol:methanol:water (2:1:1) shows an $R_f$ of 0.05 as a single spot.

Mass spectral data on the purified antihypertensive compound 176 indicates a molecular formula of $C_{11}H_{23}N_5O_7$ with a molecular weight of 349.

Field desorption (FD) mass spectral data indicates the following data:
$(M+H)^+$ 350; $(M—H_2O+H)^+$ 332

TMS derivatization of the antihypertensive compound 176 with BSTFA/pyridine at 90° C. for 3 hours yields approximately: m/e 178=349 $TMS_6$ ($D_9$-TMS m/e 835) species. Further derivitization is suggested by the following ions:

| $H_9$—TMS | $D_9$—TMS | No. TMS |
|---|---|---|
| 853 | 916 | 7 |
| 925 | 997 | 8 |
| 997 | 1078 | 9 |

High resolution mass spectral elemental compositions of the principal ions for the predominant m/e 781 (349 $TMS_6$) species are:

| m/e | No. TMS | Formula | Calc. | Found |
|---|---|---|---|---|
| 781 | 6 | $C_{12}H_{23}N_5O_7$—$T_6$ | .3973 | .3980 |
| 491 | 4 | $C_7H_{15}N_4O_3$—$T_4$ | .2728 | .2720 |
| 362 | 3 | $C_5H_8NO_4$—$T_3$ | .1640 | .1650 |
| 332 | 3 | $C_4H_{10}N_3O$—$T_3$ | .2012 | .2012 |
| 290 | 2 | $C_5H_8NO_4$—$T_2$ | .1245 | .1246 |
| 242 | 2 | $C_4H_8N_3$—$T_2$ | .1503 | .1485 |
| 216 | 2 | $C_2H_6N_3$—$T_2$ | .1347 | .1344 |

The 300 MHz proton NMR spectrum is shown in FIG. I. The spectrum was recorded at pD 5.32 in $D_2O$ at 25° C. The pD value in $D_2O$ solution is the direct pH meter reading, uncorrected for isotope effects. TSP (sodium 2,2-tetradeutero-3-trimethylsilylpropionate) was added as an internal reference.

The infrared spectrum is shown in FIG. 2. The spectrum was recorded on a KBr pellet preparation of compound 176.

On the basis of this spectroscopic data, the following structural formula has been assigned to the natural product, compound 176:

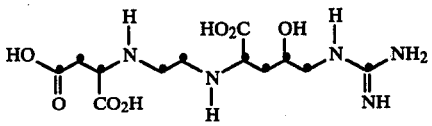

ANTIHYPERTENSIVE ACTIVITY AND ANGIOTENSIN CONVERTING ENZYME INHIBITION

(A) ENZYME

Angiotensin-converting enzyme was prepared by slicing 54 g of rat lung and homogenizing the tissue in 400 ml of a 0.10M $K_2HPO_4$—$KH_2PO_4$ buffer (pH=8.3). The homogenate was centrifuged and the supernatant was dialyzed against 4 liters of 0.01M $K_2HPO_4$—$KH_2PO_2$ buffer (pH=8.3) for 16 hours and again centrifuged. The supernatant was diluted with 2 volumes of water and 25 μl was used for the assay. The unused enzyme suspension was stored in a liquid nitrogen tank.

ASSAY PROCEDURE

To 0.5 ml of cultured broth (including mycelia) was added 0.5 ml methanol. This mixture was vortexed and centrifuged. A 10 μl sample of the broth supernatant was admixed with 0.2 ml of a reaction mixture containing:

| (A) 1 M NaCl | 10 ml |
| (B) 0.25 M $K_2HPO_4$—$KH_2PO_4$ buffer (pH = 8.3) | 5 ml |
| (C) HHL substrate γ | 5 ml |

γHHL substrate contains 20 mg of hippuryl-L-histidyl-L-leucine dissolved in 0.2 ml of 1.0N HCl and 9.6 ml $H_2O$ finally adjusted to pH=8.0 with about 0.2 ml of 1.0N NaOH.

A 25 μl aliquot of the enzyme suspension was added to the above reaction-broth mixture and incubated at 37° C. for 30 minutes. The enzyme reaction was quenched by placing the mixture in a boiling water bath for 10 minutes. A blank was prepared by adding the enzyme aliquot to the reaction mixture after the boiling water treatment. A positive control consisted of a 10 μl mixture of methanol and water (1:1). A 1.0 ml portion of 0.2M $K_2HPO_4$—$KH_2PO_4$ buffer (pH=8.3) was added to each boiled mixture and then 0.5 ml of 3% 2,4,6-trichloro-S-triazine in dioxane (3% TT) was added and the mixture vortexed. The solutions were centrifuged and the supernatant from each solution was measured for optical density (O.D.) at 382 nm. The percentage of inhibition of the angiotensin I-converting enzyme was defined by the equation:

$$\% \text{ Inhibition} = 100 \times \frac{\text{O.D. (positive control)} - \text{O.D. (test sample)}}{\text{O.D. (positive control)} - \text{O.D. (blank)}}$$

Broth samples from medium 3 (see Table I) showing at least 90% inhibition were deemed positive. For the other media listed, a minimum inhibition percentage of 80% indicated a positive result. A positive assay result indicated that the cultured broth was producing the desired compound, 176.

ANTIHYPERTENSIVE ACTIVITY

In rats, the antihypertensive compound 176 was found to possess a dose-related inhibition of the pressor response to angiotensin-I with an $ID_{50}$ of 142 mg per kg when administered intravenously.

Male Sprague-Dawley rats (250–300 g) were anesthetized with Dialurethane (1 ml/kg i.p.). The animals were vagotomized and the trachea cannulated. The right femoral vein was cannulated with PE-50 tubing for drug injections. The left carotid artery was cannulated with PE-50 tubing for blood pressure recording via a Statham P23Gb transducer connected to a Hewlett-Packard Dual Channel Carrier Amplifier recorder. The rats were pretreated with mecamylamine (1 mg/kg i.v.) and warmed on a heating pad to maintain body temperature at approximately 350° as determined by a rectal thermometer. Two rats were prepared in a similar fashion and tested simultaneously. Human synthetic angiotensin I (Beckman) was used as the standard at a dose of 100 ng/kg (stock solution, 1 μg/ml) and administered via the femoral vein in a standard volume of 100 μl/100 g body weight. 200 μl of normal saline was used to flush the angiotensin I and the test drug through the cannula.

The test procedure was as follows: angiotensin I was injected twixe at 10-minute intervals to establish the baseline response for each animal. The two responses were averaged and then utilized as the reference response for all future calculations of percent inhibition. Ten minutes later, the first dose of the converting enzyme inhibitor (compound 176) was injected at the lowest dose. Injection of angiotensin I was repeated 10 minutes later and the pressor response determined. This procedure was repeated until at least 4 doses of the converting enzyme inhibitor were tested in an increasing logarithmic fashion, i.e., 1, 3, 10, 30, etc. μg/kg. i.v. with 10 minutes between the injections of drug and angiotensin I followed 10 minutes later by the next dose of inhibitor. The doses of the converting enzyme inhibitor were not cumulated. The $ID_{50}$ was calculated based upon the % inhibition of the initial angiotensin I pressor response by means of linear regression analysis of the best fit line.

From the foregoing data, it would be expected that the antihypertensive compound 176 would have an effective daily dosage range of from 100 mg/kg to 1000 mg/kg for the treatment of hypertension in humans.

The antihypertensive compound 176 may be combined with an appropriate pharmaceutical carrier, as is well known to those skilled in the art of compounding. For purpose of injected administration whether via i.v., s.c., or i.m. routes, aqueous solutions, buffered if necessary, may be employed. Other suitable routes of administration may include oral, parenteral, and the like. Appropriate dosage forms may be exemplified by tablets, troches, dispersions, suspensions, capsules and the like. The ultimate choice of route and dosage should be made by the attending physician and based on the patient's unique condition.

Typical pharmaceutical dosage forms that may be useful for the administration of the antihypertensive compound 176 are given in the following examples.

EXAMPLE I

| Capsule Ingredients | Amount |
|---|---|
| Compound 176 | 100 mg |
| Lactose | 100 mg |

The ingredients are mixed and filled into a hard gelatin capsule.

| | |
|---|---|
| Antihypertensive Compound 176 | 100 mg |
| Sucrose | 75 mg |
| Starch | 25 mg |
| Talc | 5 mg |
| Stearic Acid | 2 mg |

The ingredients are mixed and filled into a hard gelatin capsule.

EXAMPLE II

For 100 tablets containing 100 mg of the antihypertensive compound 176:

| Tablet Ingredients | Amount |
|---|---|
| Compound 176 | 10.0 g |
| Anhydrous lactose USP | 21.7 g |
| Starch (directly compressible) | 3.0 g |
| Magnesium stearate | 0.3 g |

The ingredients are sieved through a 250 μm sieve and intimately mixed in a blender. The blended solids are compressed between 8.5 mm diameter punches in a tableting machine.

EXPERIMENTAL

The following examples illustrate the preparation and isolation of the antihypertensive compound 176.

For Examples III–VI, the following table, (k) describes the various nutrient media used to preferentially grow the microorganism Streptomyces species ATCC 39069. For convenience, the media will be referred to in the Examples as described below.

TABLE I

| NUTRIENT MEDIA COMPOSITION | |
|---|---|
| Medium (1) | |
| Dextrose | 1.0 g |
| Soluble starch | 10.0 g |
| Beef extract | 3.0 g |
| Yeast Autolysate (Ardamine) | 5.0 g |
| NZ Amine Type E | 5.0 g |
| MgSO$_4$.7H$_2$O | 0.05 g |
| Phosphate Buffer: | |
| (A) KH$_2$PO$_4$ | 0.182 g |
| (B) Na$_2$HPO$_4$ | 0.190 g |
| CaCO$_3$ | 0.5 g |
| Distilled water | 1000 ml |
| pH 7.0–7.2 (adjust with NaOH) | |
| Medium (2) | |
| Dextrose | 20.0 g |
| Bacto Peptone | 5.0 g |
| Difco Meat Extract | 5.0 g |
| NaCl | 5.0 g |
| Primary Yeast | 3.0 g |
| Distilled water | 1000 ml |
| pH 7.0 (then add 3.0 g CaCO$_3$) | |
| Medium (3) | |
| Corn steep liquor | 15.0 g |
| (NH$_4$)$_2$SO$_4$ | 4.0 g |
| CaCO$_3$ | 6.0 g |
| Soluble Starch | 20.0 g |
| Corn Meal | 1.0 g |
| Soybean Meal | 4.0 g |
| Glucose | 5.0 g |
| KH$_2$PO$_4$ | 0.3 g |
| Soybean oil | 2.5 g |
| Distilled Water | 1000 ml |
| pH 6.7 | |

EXAMPLE III

A lyophilized medium (1) sample of Streptomyces species ATCC 39069 was used to aseptically inoculate a 250 ml baffled Erlenmeyer flask containing 54 ml of seed medium (1) (see Table I). After 1 day of incubation at 28° C. with agitation at 220 rpm (2" throw) good growth was obtained.

EXAMPLE IV

A series of 2 ml samples of the broth from Example III were used to inoculate (5% inoculum) a series of 250 ml unbaffled Erlenmeyer production flasks (5) each containing 40 ml of production medium (3) (see Table I). After 4 days incubation at 28° C. with agitation of 220 rpm (2" throw), the broths were harvested and pooled.

EXAMPLE V

A lyophilized medium (1) sample of Streptomyces species ATCC 39069 was used to aseptically inoculate a 250 ml baffled Erlenmeyer flask containing 54 ml of seed medium (2) (see Table I). After 3 days of incubation at 28° C. with agitation at 220 rpm (2" throw) good growth was obtained.

EXAMPLE VI

A series of 2 ml samples of the broth from Example V were used to inoculate (5% inoculum) a series of 250 ml unbaffled Erlenmeyer flasks (5) each containing 40 ml of production medium (3) (see Table I). After 4 days incubation at 28° C. with agitation of 220 rpm (2" throw), the broths were harvested and pooled.

After cultivation, the accumulated antihypertensive compound 176 can be recovered from the cultured broth by conventional chromatographic means.

EXAMPLE VII

The pooled, harvested broth from Example VI was filtered employing a conventional filter aid such as Celite and the pH of the broth (7.5) was adjusted with 2.5N hydrochloric acid to about 3.5. The acidified broth was adsorbed onto a column of Dowex 50×4 (200–400 mesh) ammonium cycle resin and the column was washed with one bed volume of water. The column was eluted with aqueous 2% pyridine (v/v).

One bed volume of eluant was collected and concentrated in vacuo. The concentrated solution was adsorbed onto a column of Dowex 50×4 (200–400 mesh) pyridinium cycle resin and the column was eluted stepwise with pyridinium acetate buffers of increasing pH. The pH range began at about 3.5 and increased by 0.1 pH units every bed volume of elution. The active component, compound 176 was eluted from the column between pH 4.0 and 4.5.

The combined active pyridinium acetate fractions were concentrated in vacuo to about one-half volume and cooled in an ice bath. The antihypertensive compound, 176 crystallized from this cooled solutions and was recovered by filtration, as colorless needles.

Claims of the invention to follow.

What is claimed is:

1. The antihypertensive compound 176 having the structural formula:

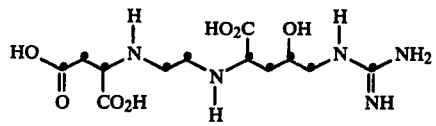

and which has the following chemical-physical characteristics in its essentially pure form:
(a) crystalline compound—needles from cold water,
(b) tlc (butanol:methanol:water—2:1:1) on silica gel; single spot $R_f=0.05$,
(c) UV (100 µg/ml)—end only adsorption,
(d) moderate solubility in water and aqueous lower alkanol solutions,
(e) insolubility in the lower alkanols and apolar solvents,
(f) mass spectral data on the purified antihypertensive compound 176 indicates a molecular formula of $C_{12}H_{23}N_5O_7$ with a molecular weight of 349;
(g) field adsorption (FD) mass spectral data indicates the following data: $(M+H)^+ 350$; $(M-H_2O+H)^+ 332$
(h) TMS derivatization with BSTFA/pyridine at 90° C. for 3 hours yields predominantly: M/e 781=349 $TMS_6$ ($D_9$-TMS m/e 835) species; further derivitization is suggested by the following ions:

| $H_9$—TMS | $D_9$—TMS | No. TMS |
|---|---|---|
| 853 | 916 | 7 |
| 925 | 997 | 8 |
| 997 | 1078 | 9 |

(i) high resolution mass spectral elemental compositions of the principal ions for the predominant m/e 781 349 $TMS_6$) species are:

| m/e | No. TMS | Formula | Calc. | Found |
|---|---|---|---|---|
| 781 | 6 | $C_{12}H_{23}N_5O_7$—$T_6$ | .3973 | .3980 |
| 491 | 4 | $C_7H_{15}N_4O_3$—$T_4$ | .2728 | .2720 |
| 362 | 3 | $C_5H_8NO_4$—$T_3$ | .1640 | .1650 |
| 332 | 3 | $C_4H_{10}N_3O$—$T_3$ | .2012 | .2012 |
| 290 | 2 | $C_5H_8NO_4$—$T_2$ | .1245 | .1246 |
| 242 | 2 | $C_4H_8N_3$—$T_2$ | .1503 | .1485 |
| 216 | 2 | $C_2H_6N_3$—$T_2$ | .1347 | .1344 |

(j) the 300 MHz proton NMR spectrum shown in FIG. 1;
(k) the infrared spectrum shown in FIG. 2.

2. A pharmaceutical composition for treating hypertension in humans comprising an effective amount of the antihypertensive compound 176 of claim 1 and a pharmaceutical carrier.

3. A method of treating hypertension in humans which comprises administering an effective amount of the antihypertensive compound 176 in a pharmaceutically acceptable carrier, said antihypertensive compound 176 having the structural formula:

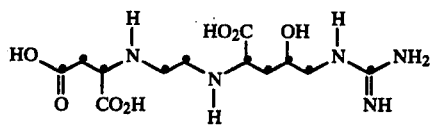

and which has the following chemical-physical characteristics in its essentially pure form:
(a) crystalline compound—needles from cold water,
(b) tlc (butanol:methanol:water—2:1:1) on silica gel; single spot $R_f=0.05$,
(c) UV (100 µg/ml)—end only adsorption,
(d) moderate solubility in water and aqueous lower alkanol solutions,
(e) insolubility in the lower alkanols and apolar solvents,
(f) mass spectral data on the purified antihypertensive compound 176 indicates a molecular formula of $C_{12}H_{23}N_5O_7$ with a molecular weight of 349;
(g) field desorption (FD) mass spectral data indicates the following data: $(M+H)^+ 350$; $(M-H_2O+H)^+ 332$
(h) TMS derivatization with BSTFA/pyridine at 90° C. for 3 hours yields predominantly: M/e 781=349 $TMS_6$ ($D_9$-TMS m/e 835) species;
further derivitization is suggested by the following ions:

| $H_9$—TMS | $D_9$—TMS | No. TMS |
|---|---|---|
| 853 | 916 | 7 |
| 925 | 997 | 8 |
| 997 | 1078 | 9 |

(i) high resolution mass spectral elemental compositions of the principal ions for the predominant m/e 781 (349 $TMS_6$) species are:

| m/e | No. TMS | Formula | Calc. | Found |
|---|---|---|---|---|
| 781 | 6 | $C_{12}H_{23}N_5O_7$—$T_6$ | .3973 | .3980 |
| 491 | 4 | $C_7H_{15}N_4O_3$—$T_4$ | .2728 | .2720 |
| 362 | 3 | $C_5H_8NO_4$—$T_3$ | .1640 | .1650 |
| 332 | 3 | $C_4H_{10}N_3O$—$T_3$ | .2012 | .2012 |
| 290 | 2 | $C_5H_8NO_4$—$T_2$ | .1245 | .1246 |
| 242 | 2 | $C_4H_8N_3$—$T_2$ | .1503 | .1485 |
| 216 | 2 | $C_2H_6N_3$—$T_2$ | .1347 | .1344 |

(j) the 300 MHz proton NMR spectrum shown in FIG. 1;
(k) the infrared spectrum shown in FIG. 2.

* * * * *

UNITED STATES PATENT AND TRADEMARK OFFICE
CERTIFICATE OF CORRECTION

PATENT NO. : 4,464,395
DATED : August 7, 1984
INVENTOR(S) : LEEYUAN HUANG

It is certified that error appears in the above—identified patent and that said Letters Patent is hereby corrected as shown below:

Column 9, Claim 1, line 31, "adsorption" should be

-- desorption --

Signed and Sealed this

Eighth Day of January 1985

[SEAL]

Attest:

Attesting Officer

GERALD J. MOSSINGHOFF

Commissioner of Patents and Trademarks